(12) United States Patent
Buckley et al.

(10) Patent No.: US 10,617,514 B2
(45) Date of Patent: Apr. 14, 2020

(54) BIASED ENDOLUMINAL DEVICE

(75) Inventors: Kyle R. Buckley, Flagstaff, AZ (US);
Vincent L. Perko, Flagstaff, AZ (US)

(73) Assignee: W. L. Gore & Associates, Inc.,
Newark, DE (US)

( * ) Notice: Subject to any disclaimer, the term of this patent is extended or adjusted under 35 U.S.C. 154(b) by 0 days.

(21) Appl. No.: 13/330,522

(22) Filed: Dec. 19, 2011

(65) Prior Publication Data
US 2012/0323304 A1 Dec. 20, 2012

Related U.S. Application Data

(60) Provisional application No. 61/425,882, filed on Dec. 22, 2010.

(51) Int. Cl.
*A61F 2/07* (2013.01)
*A61F 2/95* (2013.01)
*A61F 2/89* (2013.01)

(52) U.S. Cl.
CPC ............... *A61F 2/07* (2013.01);
*A61F 2/89* (2013.01); *A61F 2002/072* (2013.01); *A61F 2002/075* (2013.01); *A61F 2002/9522* (2013.01); *A61F 2230/005* (2013.01); *A61F 2230/0019* (2013.01); *Y10T 29/49863* (2015.01)

(58) Field of Classification Search
USPC .............. 623/1.35, 1.18, 1.32–1.33
See application file for complete search history.

(56) References Cited

U.S. PATENT DOCUMENTS

| | | | |
|---|---|---|---|
| 5,922,019 A | 7/1999 | Hankh et al. | |
| 6,110,198 A | 8/2000 | Fogarty | |
| 6,120,534 A | 9/2000 | Ruiz | |
| 6,139,573 A | 10/2000 | Sogard | |
| 6,203,735 B1 | 3/2001 | Edwin | |
| 6,352,561 B1 | 3/2002 | Leopold et al. | |
| 6,355,057 B1 * | 3/2002 | DeMarais | A61F 2/91 623/1.15 |
| 6,395,212 B1 | 5/2002 | Solem | |
| 6,551,350 B1 | 4/2003 | Thornton et al. | |
| 6,635,083 B1 * | 10/2003 | Cheng et al. | 623/1.15 |
| 6,729,356 B1 | 5/2004 | Baker et al. | |
| 6,773,454 B2 | 8/2004 | Wholey et al. | |
| 6,981,982 B2 | 1/2006 | Armstrong et al. | |
| 7,731,744 B1 * | 6/2010 | Cox | 623/1.14 |

(Continued)

FOREIGN PATENT DOCUMENTS

| | | |
|---|---|---|
| WO | 97/33532 | 9/1997 |
| WO | 199826731 A2 | 6/1998 |
| WO | WO-2001024733 A1 | 4/2001 |

OTHER PUBLICATIONS

International Search Report and Written Opinion from PCT/US2018/015736, dated Apr. 17, 2018, 10 pages.

*Primary Examiner* — Leslie Lopez

(57) ABSTRACT

An endoluminal device can comprise a flexible tubular wall and a frame member. The frame member can be comprised of a shape-memory material having sides with protrusions which are partially or substantially flattened when formed together with the flexible tubular wall to thereby create a bias in the side wall of the endoluminal device that resists deformation from a desired device profile during crush loading and is thereby resistant to invaginations when deployed.

7 Claims, 2 Drawing Sheets

(56) References Cited

U.S. PATENT DOCUMENTS

| | | | |
|---|---|---|---|
| 2001/0053929 A1* | 12/2001 | Vonesh | A61F 2/07 623/1.12 |
| 2006/0052865 A1 | 3/2006 | Banas | |
| 2008/0071356 A1 | 3/2008 | Greenhalgh et al. | |
| 2008/0288044 A1* | 11/2008 | Osborne | 623/1.13 |
| 2009/0048662 A1 | 2/2009 | Pavcnik et al. | |

* cited by examiner

BIASED ENDOLUMINAL DEVICE

CROSS REFERENCE TO RELATED APPLICATIONS

This application is a non-provisional of, and claims priority to, U.S. Provisional Patent Application No. 61/425,882, entitled "Deployment of Endoluminal Devices," filed Dec. 22, 2010, the content of which is hereby incorporated by reference in its entirety.

BACKGROUND

Field

The present disclosure relates to improved expandable endoluminal devices for treating disease of the vasculature.

Discussion of the Related Art

To facilitate delivery to a treatment site, an expandable endoluminal device (e.g., a stent graft) can be crush loaded over a tubular element and retained by a sheath or other tubular element. Once delivered through the tortuous vasculature, deployment of the endoluminal device from the delivery device occurs at the treatment site.

Crushing can, in some instances, result in infolds in or invagination of the endoluminal device, especially where its cross sectional profile is not curved, as is sometimes the case in a bifurcation portion or an otherwise tapered portion.

It remains desirable to provide endoluminal devices that are resistant to infolding or invagination during crushing, as well as methods for making the same.

DETAILED DESCRIPTION

Figure 1:
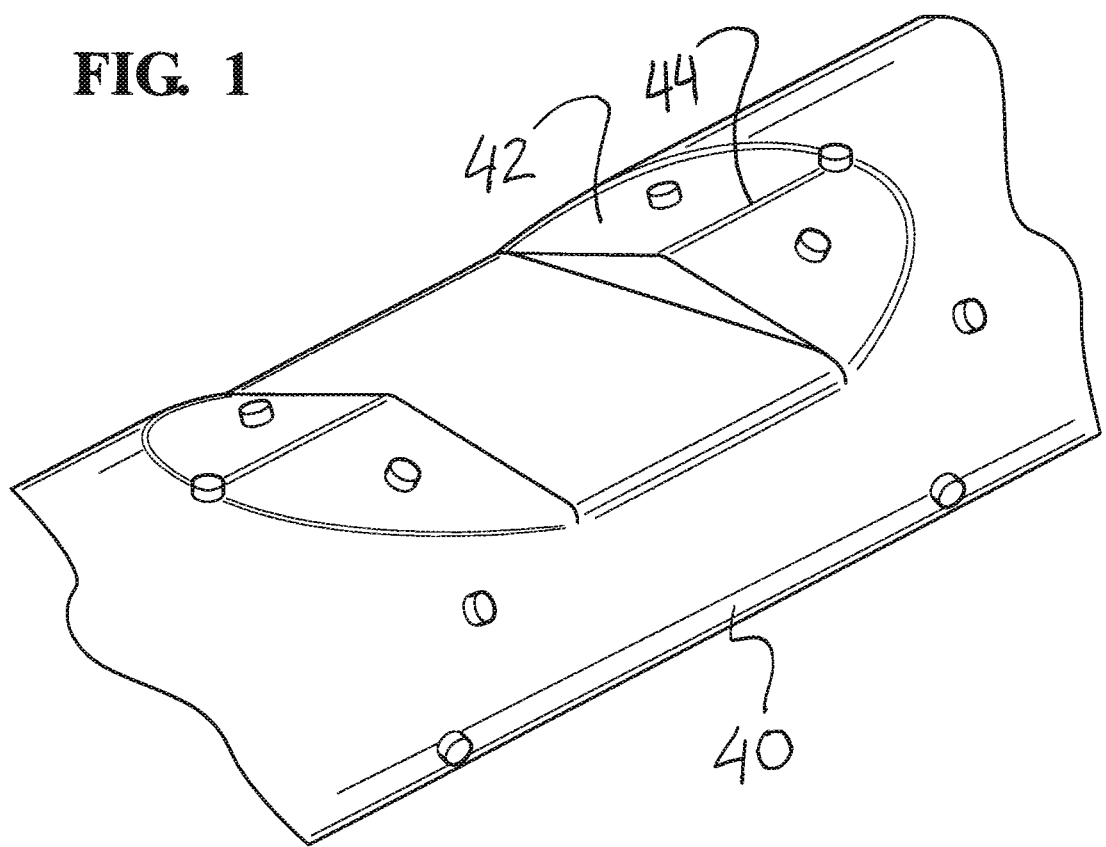
FIG. 1 illustrates in accordance with various embodiments a mandrel for forming a wire stent or frame member for endoluminal devices.

Persons skilled in the art will readily appreciate that various aspects of the present disclosure can be realized by any number of methods and apparatuses configured to perform the intended functions. Stated differently, other methods and apparatuses can be incorporated herein to perform the intended functions. It should also be noted that the accompanying drawing figures referred to herein are not all drawn to scale, but can be exaggerated to illustrate various aspects of the present disclosure, and in that regard, the drawing figures should not be construed as limiting. Finally, although the present disclosure can be described in connection with various principles and beliefs, the present disclosure should not be bound by theory.

An endoluminal device, in accordance with various embodiments, comprises a flexible tubular wall and a frame member having a bias for resisting deformation of the tubular wall, such as infolding or invagination, from a desired profile.

An endoluminal device, in accordance with various embodiments, can be any stent graft comprising a portion with a cross sectional profile having a desired profile and a structural bias that maintains the desired cross sectional profile of the device, for example, during deployment of the device along tortuous anatomy.

An endoluminal device, in accordance with various embodiments, can, for example, have a substantially uncurved section in a bifurcation portion or an otherwise tapered portion where the stent graft transitions from a larger perimeter to a smaller perimeter.

In various embodiments, a frame member includes a stent suitable for the treatment of vascular conditions, such as an abdominal aortic aneurism, and can provide structural support for the flexible tubular wall of the endoluminal device and/or the vasculature. A frame member can be comprised either of a wire have a helical configuration or be comprised of one or a plurality of rings. Among other configurations, the wire or a ring itself can be linear or have a sinusoidal or zig-zag pattern. Still other various embodiments of the frame member can be cut from a tube and have any pattern suitable for the treatment.

In various embodiments, the frame member comprises a shape-memory material, such as nitinol. In various embodiments, the frame member can be comprised of other materials, self-expandable or otherwise expandable (e.g., with a balloon or spring mechanism), such as various metals (e.g., stainless steel), alloys and polymers.

In various embodiments, a frame member includes one or more protrusions for creating a bias when the frame member is assembled with and/or between graft layers to form the endoluminal device. In general, a protrusion includes any elevation, ridge, projection, recession, indentation or other outwardly or inwardly extending feature that, while not assembled with a graft layer and/or between graft layers, is substantially different vis-à-vis the endoluminal device.

In various embodiments, the protrusion can be characterized by the frame member defining a lumen comprising a portion (e.g., a peripheral or an intermediate portion) having a cross-sectional area larger or smaller than that of the corresponding portion of the flexible tubular wall and/or the endoluminal device. The cross-sectional shape can be a pentagon, octagon or any other suitable shape.

In various embodiments, the frame member is configured to have convex or outwardly extending protrusions. However, a protrusion can be generally configured in any direction an internal structural bias is desired in the endoluminal device.

Protrusions can be manufactured into the frame member or otherwise introduced post manufacture. In various embodiments, a suitable bias can be achieved by a protrusion that is from about 5% to about 25% of a desired diameter or width of the flexible tubular wall and/or the endoluminal device. An endoluminal device can, for example, be made with a frame member having a protrusion that is about 10% of the diameter or width of the flexible tubular wall and/or endoluminal device, Generally, a larger protrusion dimension relative to the desired diameter or width of the flexible tubular wall and/or endoluminal device results in a higher bias for resisting infolding or invagination of the endoluminal device at or near the protrusion.

In various embodiments, a flexible tubular wall is generally any abluminal and/or luminal covering configured to partially or substantially smooth, flatten, or otherwise lessen the frame member protrusion and thereby bring the frame member protrusion into conformity with the desired dimension and profile of the endoluminal device.

In various embodiments, the shape of the frame is generally conical and is constrained toward a substantially cylindrical shape by the flexible tubular wall. In various embodiments, a flexible tubular wall defines a surface that does not include a protrusion present in the frame member. In various embodiments, a portion of a flexible tubular wall (e.g., a peripheral or an intermediate portion) has a cross-sectional area that does not include protrusion present in the corresponding portion of the frame member.

In various embodiments, a flexible tubular wall comprises taped ePTFE. Other useful materials for the flexible tubular wall can comprise one or more of nylons, polycarbonates, polyethylenes, polypropylenes, polytetrafluoroethylenes, polyvinyl chlorides, polyurethanes, polysiloxanes, and other biocompatible materials.

In various embodiments, a flexible tubular wall is fixedly secured or otherwise coupled at a single or a plurality of locations to the abluminal or luminal surface of the frame member, for example, using heat shrinking, adhesion or other processes known in the art. In various embodiments, the flexible tubular wall is coupled to an anchor extending outwardly from the frame and being generally proximal to the frame protrusion. In various embodiments, a plurality of flexible tubular walls are used, the walls being coupled to both the abluminal and luminal surfaces of the frame member.

Various embodiments comprise one or more flexible tubular walls that are coupled to the frame member at, along or near the frame member protrusion to partially or substantially smooth, flatten, or otherwise lessen the frame member protrusion and thereby create an internal structural bias in the direction of the protrusion when the device is in an unconstrained state.

In various embodiments, frame member protrusion is partially or substantially flattened when coupled to or otherwise formed together with the flexible tubular wall. Flattening the protrusion of the frame member can create a structural bias in the endoluminal device that resists radial deformation (e.g., infolding or invagination) in a direction substantially opposite the protrusion, or that otherwise resists deformation from its cross-sectional shape, during crush loading and maintains its structural integrity when deployed and the device is in an unconstrained state.

In various embodiments, the endoluminal device has a resistance to radial deformation which varies circumferentially or peripherally about a cross section generally normal to a longitudinal axis of its lumen. The resistance can peak at a middle portion where one or more flexible tubular walls are coupled to the frame member.

In various embodiments, methods for making a biased endoluminal device can comprise forming the frame member on a first mandrel having a surface that includes one or more protrusions as compared to the desired profile of the endoluminal device at or near the protrusion. The endoluminal device can then be formed by wrapping the flexible tubular wall about the frame member on a second mandrel not including the protrusions and subsequently heat shrinking the flexible tubular wall to the frame member.

An exemplary endoluminal device can thereafter be radially crush loaded with a reduced likelihood of there being undesired deformation, such as infolding or invagination. A supporting balloon can be introduced into the lumen of the endoluminal device and deflated during radial crush loading to further minimize any likelihood unwanted deformation.

Various embodiments of the present disclosure are described with reference to FIGS. 1, 2, 3 and 4. Specifically, with reference to FIG. 1, a mandrel 40 for forming a frame member, such as a stent, is provided having a tapered portion 42 where the device transitions from a larger perimeter to a smaller perimeter. Tapered portion 42 can comprise a 0.05 inch ridge protrusion 44, for example. However, smaller or larger protrusions, as well as differently shaped protrusions, can be used depending on the frame shape and amount of structural bias desired.

Figure 2:
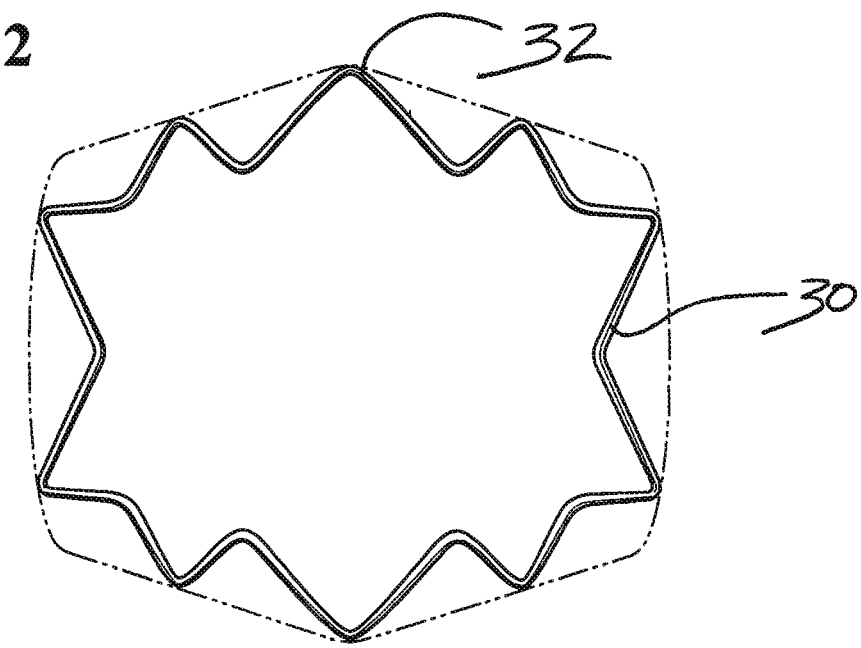
FIG. 2 illustrates an end view of a stent or frame member in accordance with various embodiments.
Figure 3:
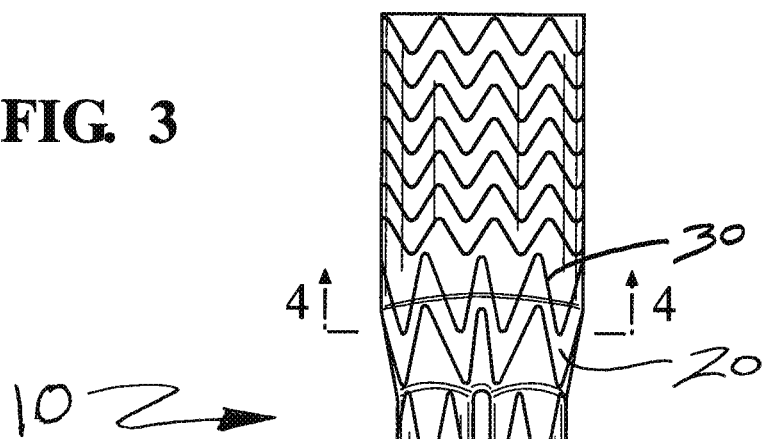
FIG. 3 illustrates a front elevational view of an endoluminal device in accordance with various embodiments.
Figure 4:
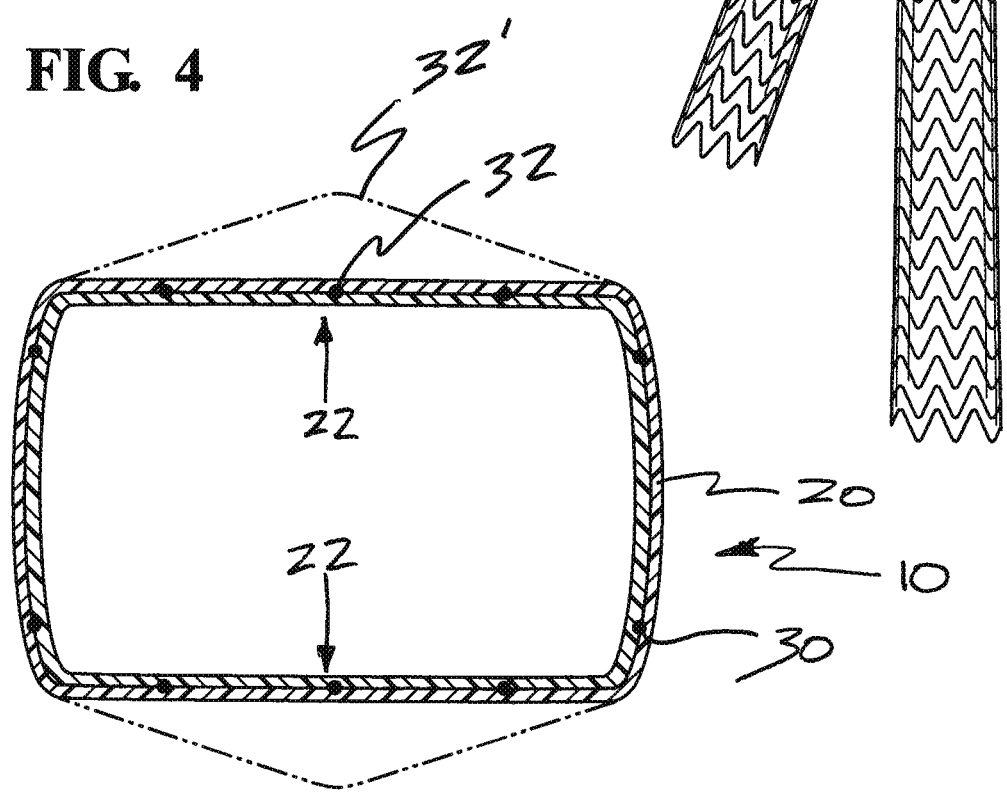
FIG. 4 is a cross-sectional of the endoluminal device in FIG. 3, in accordance with various embodiments, illustrating outward structural bias for resisting deformation during crushing and deployment.

A nitinol stent frame member 30 is wound over mandrel 40, thus creating a corresponding 0.05 inch ridge protrusion 32 in the tapered portion of frame member 30, as shown illustratively in the end view of FIG. 2. Frame member 30 is then wrapped with an ePTFE flexible tubular wall 20 to flatten ridge protrusion 32. The resulting endoluminal device 10 is shown in FIGS. 3 and 4. For ease of comparison, the dotted line 32' in FIG. 4 illustrates the profile of the frame member assembled with a graft layer and/or between graft layers to form the device. Thus, it should be readily appreciated that the difference in profiles or positions between the unconstrained frame member 32' prior to device assembly and the frame member along the protrusion 32 after assembly with a graft layer and/or between graft layers generally represents a structural bias that resists infolding or invagination of the device along the portion of the frame member having the protrusion.

Endoluminal device 10 can be radially crush loaded with a radial crusher. Because of the internal structural bias (depicted as reference numeral 22 in FIG. 4) provided by the protrusion 32, the tapered portion resists inward deflection under the squeezing force of the radial crusher. Endoluminal device 10 is then retained by a sheath or other tubular element, delivered through the tortuous vasculature and deployed at the treatment site with no infolding or invagination.

Stents having protrusions for creating a structural bias the resists deformation of an endoluminal device from a desired profile, in accordance with various embodiments, can be fabricated, for example, from cut tubes, wound wires (or ribbons) or flat patterned sheets rolled into a tubular form. Stents can be formed from metallic, polymeric or natural materials and can comprise conventional medical grade materials such as nylon, polyacrylamide, polycarbonate, polyethylene, polyformaldehyde, polymethylmethacrylate, polypropylene, polytetrafluoroethylene, polytrifluorochlorethylene, polyvinylchloride, polyurethane, elastomeric organosilicon polymers; metals such as stainless steels, cobalt-chromium alloys and nitinol and biologically derived materials such as bovine arteries/veins, pericardium and collagen. Stents can also comprise bioresorbable materials such as poly(amino acids), poly(anhydrides), poly(caprolactones), poly(lactic/glycolic acid) polymers, poly(hydroxybutyrates) and poly(orthoesters).

Potential materials for a graft member include, for example, expanded polytetrafluoroethylene (ePTFE), polyester, polyurethane, fluoropolymers, such as perfouorelastomers and the like, polytetrafluoroethylene, silicones, urethanes, ultra high molecular weight polyethylene, aramid fibers, and combinations thereof. One preferred embodiment for a graft material is ePTFE. Other embodiments for a graft member material can include high strength polymer fibers such as ultra high molecular weight polyethylene fibers (e.g., Spectra®, Dyneema Purity®, etc.) or aramid fibers (e.g., Technora®, etc.). The graft member can include a bioactive agent. In one embodiment, an ePTFE graft includes a carbon component along a blood contacting surface thereof.

Typical materials used to construct catheters for endoluminal delivery of devices, as discussed above, can comprise commonly known materials such as Amorphous Commodity Thermoplastics that include Polymethyl Methacrylate (PMMA or Acrylic), Polystyrene (PS), Acrylonitrile Butadiene Styrene (ABS), Polyvinyl Chloride (PVC), Modified Polyethylene Terephthalate Glycol (PETG), Cellulose Acetate Butyrate (CAB); Semi-Crystalline Commodity Plastics that include Polyethylene (PE), High Density Polyethylene (HDPE), Low Density Polyethylene (LDPE or LLDPE), Polypropylene (PP), Polymethylpentene (PMP); Amorphous Engineering Thermoplastics that include Polycarbonate (PC), Polyphenylene Oxide (PPO), Modified Polyphenylene Oxide (Mod PPO), Polyphenelyne Ether (PPE), Modified Polyphenelyne Ether (Mod PPE), Thermoplastic Polyurethane (TPU); Semi-Crystalline Engineering Thermoplastics that include Polyamide (PA or Nylon), Polyoxymethylene (POM or Acetal), Polyethylene Terephthalate (PET, Thermoplastic Polyester), Polybutylene Terephthalate (PBT, Thermoplastic Polyester), Ultra High Molecular Weight Polyethylene (UHMW-PE); High Performance Thermoplastics that include Polyimide (PI, Imidized Plastic), Polyamide Imide (PAI, Imidized Plastic), Polybenzimidazole (PBI, Imidized Plastic); Amorphous High Performance Thermoplastics that include Polysulfone (PSU), Polyetherimide (PEI), Polyether Sulfone (PES), Polyaryl Sulfone (PAS); Semi-Crystalline High Performance Thermoplastics that include Polyphenylene Sulfide (PPS), Polyetheretherketone (PEEK); and Semi-Crystalline High Performance Thermoplastics, Fluoropolymers that include Fluorinated Ethylene Propylene (FEP), Ethylene Chlorotrifluroethylene (ECTFE), Ethylene, Ethylene Tetrafluoroethylene (ETFE), Polychlortrifluoroethylene (PCTFE), Polytetrafluoroethylene (PTFE), Polyvinylidene Fluoride (PVDF), Perfluoroalkoxy (PFA). Other commonly known medical grade materials include elastomeric organosilicon polymers, polyether block amide or thermoplastic copolyether (PEBAX) and metals such as stainless steel and nickel/titanium alloys.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:
1. An endoluminal device comprising:
a flexible tubular wall defining a lumen having a first peripheral cross-sectional shape; and
a frame member formed of at least one wire and having a second peripheral cross-sectional shape different than the first peripheral cross-sectional shape, the frame member being coupled to the flexible tubular wall to provide structural support, the second peripheral cross-sectional shape being larger than the first peripheral cross-sectional shape,
wherein the at least one wire includes a first portion of the frame member and a second portion of the frame member that is fixedly secured between layers of the flexible tubular wall to continuously bias the second portion of the frame member to form a deformed portion of the frame while the device is in an unconstrained state to resist deformation of the lumen from the first peripheral cross-sectional shape during deployment, resist infolding or invagination in a crushed state and deploy to a deployed state with no infolding or invagination, wherein the resistance to deformation varies circumferentially about a cross section normal to a longitudinal axis of the frame member;
wherein prior to the first portion of the frame member being fixedly secured to the tubular wall, the at least one wire of the frame member has a sinusoidal shape and the first portion is free from any radially outwardly extending protrusion such that the first portion of the frame member has a cross-sectional area prior to being fixedly secured to a first, corresponding portion of the tubular wall that is the same as the cross-sectional area of the first, corresponding portion of the tubular wall,
wherein prior to the second portion of the frame member being fixedly secured to a second, corresponding portion of the tubular wall, the second portion of the frame member has a sinusoidal shape and includes a radially outwardly extending protrusion that extends outwardly from a remaining portion of the frame relative to the lumen in a first configuration, such that the second portion has a cross-sectional area prior to being fixedly secured to the second, corresponding portion of the tubular wall that is larger than the cross-sectional area of the second, corresponding portion of the tubular wall, the protrusion has a length that is 5% to 25% of a diameter or width of the flexible tubular wall or the endoluminal device and the protrusion is deformed radially inwardly in a second configuration, maintaining the sinusoidal shape, by the layers of the flexible tubular wall fixedly secured thereto to create a bias and resistance to invagination of the endoluminal device that is higher along the deformed portion of the frame than the remaining portion of the frame along the cross section, the sinusoidal shape having struts between peaks and valleys.

2. The endoluminal device as set forth in claim 1, wherein the resistance to radial deformation peaks generally at a middle portion of where the flexible tubular wall is fixedly secured to the second portion of the frame member.

3. The endoluminal device as set forth in claim 2, wherein the resistance to radial deformation peaks at a plurality of locations circumferentially about the frame member.

4. An endoluminal device comprising:
a frame formed of at least one wire having a second peripheral cross-sectional shape being larger than a first peripheral cross-sectional shape;
a flexible tubular wall forming a first lumen having a predefined peripheral cross-sectional shape bifurcating into a second and third lumen, the flexible tubular wall being fixedly secured to the frame and deforming the frame from an initial manufactured shape such that the deformed frame resists deformation of the flexible tubular wall during deployment from a crushed state to a deployed state and is configured to resist in folding or invagination in the crush state and deploy without in folding or invagination in the deployed state, wherein the resistance to deformation varies circumferentially about a cross section normal to a longitudinal axis of the frame,
wherein the initial manufactured shape of the frame along the cross section includes a sinusoidal shape having a radially outwardly extending protrusion that extends outwardly from a remaining portion of the frame at the cross section relative to the lumen in the initial manufactured shape and has a length that is 5% to 25% of a diameter of the endoluminal device;
wherein the radially outwardly extending protrusion is deformed radially inwardly in a second configuration, maintaining the sinusoidal shape, and is fixedly secured between layers of the flexible tubular wall to create a bias and resistance to invagination of the endoluminal device that is higher along the deformed frame than the remaining portion of the frame along the cross section, the frame maintaining the sinusoidal shape in the second configuration, wherein the sinusoidal shape includes struts between peaks and valleys.

5. The endoluminal device as set forth in claim 4, wherein the initial manufactured shape of the frame is conical.

6. The endoluminal device as set forth in claim 5, wherein the flexible tubular wall is fixedly secured to the frame and constrains the frame toward a cylindrical shape.

7. The endoluminal device as set forth in claim 4 including an anchor extending outwardly from the frame and being proximal to the protrusion.

* * * * *